US008473075B2

(12) United States Patent
Gallegos et al.

(10) Patent No.: US 8,473,075 B2
(45) Date of Patent: Jun. 25, 2013

(54) COCHLEAR IMPLANT SYSTEM WITH REMOVABLE STYLET

(75) Inventors: Rosa Gallegos, Sylmar, CA (US); Chuladatta Thenuwara, Castaic, CA (US)

(73) Assignee: Advanced Bionics, Valencia, CA (US)

( * ) Notice: Subject to any disclaimer, the term of this patent is extended or adjusted under 35 U.S.C. 154(b) by 396 days.

(21) Appl. No.: 12/823,380

(22) Filed: Jun. 25, 2010

(65) Prior Publication Data
US 2011/0319907 A1    Dec. 29, 2011

(51) Int. Cl.
*A61N 1/05*    (2006.01)
(52) U.S. Cl.
CPC .................................... *A61N 1/0541* (2013.01)
USPC .............................. 607/137; 607/57; 600/379
(58) Field of Classification Search
USPC ........................ 600/379, 585; 607/55–57, 137
See application file for complete search history.

(56) References Cited

U.S. PATENT DOCUMENTS

| | | |
|---|---|---|
| 5,437,632 A | 8/1995 | Engelson |
| 5,470,322 A | 11/1995 | Horzewski et al. |
| 5,476,497 A | 12/1995 | Mower et al. |
| 5,573,520 A | 11/1996 | Schwartz et al. |
| 5,630,839 A | 5/1997 | Corbett et al. |
| 5,653,742 A | 8/1997 | Parker et al. |
| 5,762,630 A | 6/1998 | Bley et al. |
| 5,800,500 A | 9/1998 | Spelman et al. |
| 5,999,859 A | 12/1999 | Jolly |
| 6,048,338 A | 4/2000 | Larson et al. |
| 6,119,044 A | 9/2000 | Kuzma et al. |
| 6,125,302 A | 9/2000 | Kuzma |
| 6,321,125 B1 | 11/2001 | Kuzma |
| 6,368,316 B1 | 4/2002 | Jansen et al. |

(Continued)

FOREIGN PATENT DOCUMENTS

| | | |
|---|---|---|
| EP | 1341578 B1 | 4/2002 |
| EP | 2209520 A1 | 7/2003 |

(Continued)

OTHER PUBLICATIONS

Rebscher et al, Strategies to Improve Electrode Positioning and Safety in Cochlear Implants, IEEE Trans Biomed Eng, 46(3) 340-352, 1999.

(Continued)

*Primary Examiner* — Carl H Layno
*Assistant Examiner* — Eugene Wu
(74) *Attorney, Agent, or Firm* — Steven L. Nichols; Van Cott, Bagley, Cornwall & McCarthy P.C.

(57) ABSTRACT

A cochlear implant system includes a cochlear electrode array which has a flexible body with a distal end, a plurality of electrodes supported along a length of the flexible body, and a lumen formed in the flexible body. The cochlear implant system also includes a stiffening stylet which is fully inserted into the lumen prior to insertion of the electrode array into the cochlea. The stiffening stylet is configured such the stylet does not extend to the distal end of the flexible body and remains stationary within the lumen to prevent buckling of the electrode array during insertion of the electrode array through a cochleostomy and into the cochlea. The stiffening stylet is configured to be withdrawn from the lumen after the electrode array is positioned within the cochlea. A method for implanting an electrode array into a cochlea is also provided.

23 Claims, 11 Drawing Sheets

U.S. PATENT DOCUMENTS

| | | |
|---|---|---|
| 6,421,569 B1 | 7/2002 | Treaba et al. |
| 6,428,489 B1 | 8/2002 | Jacobsen et al. |
| 6,475,209 B1 | 11/2002 | Larson et al. |
| 6,556,873 B1 | 4/2003 | Smits |
| 6,562,021 B1 | 5/2003 | Derbin et al. |
| 6,604,283 B1 | 8/2003 | Kuzma |
| 6,757,970 B1 | 7/2004 | Kuzma et al. |
| 6,858,680 B2 | 2/2005 | Gunatillake et al. |
| 6,887,235 B2 | 5/2005 | O'Connor et al. |
| 6,968,238 B1 | 11/2005 | Kuzma |
| 6,999,821 B2 | 2/2006 | Jenney et al. |
| 7,047,081 B2 | 5/2006 | Kuzma |
| 7,050,858 B1 | 5/2006 | Kuzma et al. |
| 7,063,708 B2 | 6/2006 | Gibson et al. |
| 7,066,931 B2 | 6/2006 | O'Connor et al. |
| 7,115,183 B2 | 10/2006 | Larson et al. |
| 7,146,227 B2 | 12/2006 | Dadd et al. |
| 7,239,923 B1 | 7/2007 | Tockman et al. |
| 7,269,461 B2 | 9/2007 | Dadd et al. |
| 7,272,449 B2 | 9/2007 | Dadd et al. |
| 7,315,763 B2 | 1/2008 | Kuzma et al. |
| 7,319,906 B2 | 1/2008 | Kuzma et al. |
| 7,328,072 B2 | 2/2008 | Milojevic et al. |
| 7,389,148 B1 | 6/2008 | Morgan |
| 7,403,823 B1 | 7/2008 | Kroll et al. |
| 7,451,000 B2 | 11/2008 | Gibson et al. |
| 7,540,865 B2 | 6/2009 | Griffin et al. |
| 7,571,012 B2 | 8/2009 | Gibson |
| 7,742,827 B2 | 6/2010 | Lenarz et al. |
| 2002/0029074 A1* | 3/2002 | Treaba et al. ............ 607/137 |
| 2003/0040684 A1 | 2/2003 | Soukup |
| 2003/0045921 A1 | 3/2003 | Dadd et al. |
| 2003/0093139 A1 | 5/2003 | Gibson et al. |
| 2003/0181967 A1 | 9/2003 | Dadd et al. |
| 2004/0030376 A1 | 2/2004 | Gibson et al. |
| 2004/0078057 A1 | 4/2004 | Gibson |
| 2004/0127968 A1 | 7/2004 | Kuzma et al. |
| 2004/0220651 A1* | 11/2004 | Kuzma et al. ............ 607/137 |
| 2005/0234535 A1 | 10/2005 | Risi et al. |
| 2005/0256561 A1* | 11/2005 | Gantz et al. ............ 607/137 |
| 2006/0085055 A1 | 4/2006 | Dadd et al. |
| 2006/0089569 A1 | 4/2006 | Soukup et al. |
| 2006/0235500 A1 | 10/2006 | Gibson et al. |
| 2007/0073371 A1 | 3/2007 | Dadd et al. |
| 2007/0127745 A1 | 6/2007 | Gibson et al. |
| 2007/0162098 A1 | 7/2007 | Risi et al. |
| 2008/0027527 A1 | 1/2008 | Kuzma et al. |
| 2008/0077049 A1 | 3/2008 | Hirshman |
| 2008/0109011 A1 | 5/2008 | Thenuwara et al. |
| 2008/0269864 A1 | 10/2008 | Dadd et al. |
| 2009/0030483 A1* | 1/2009 | Risi et al. ............ 607/57 |
| 2009/0043358 A1 | 2/2009 | Dadd et al. |
| 2009/0043369 A1 | 2/2009 | Radeloff |
| 2009/0043370 A1 | 2/2009 | Gibson et al. |
| 2009/0165921 A1 | 7/2009 | Kaiser |
| 2009/0312769 A1 | 12/2009 | Dadd et al. |
| 2010/0057180 A1 | 3/2010 | Gibson et al. |
| 2010/0106232 A1 | 4/2010 | Dadd et al. |
| 2010/0204768 A1 | 8/2010 | Jolly et al. |
| 2010/0287770 A1 | 11/2010 | Dadd et al. |
| 2011/0016710 A1 | 1/2011 | Dadd |

FOREIGN PATENT DOCUMENTS

| | | |
|---|---|---|
| EP | 1604626 A2 | 12/2005 |
| EP | 1604626 A3 | 12/2005 |
| EP | 1189560 B1 | 3/2006 |
| EP | 1604626 B1 | 12/2008 |
| EP | 2042137 A1 | 4/2009 |
| WO | 9306698 | 4/1993 |
| WO | 9710784 | 3/1997 |
| WO | 0071063 | 11/2000 |
| WO | 0228474 | 4/2001 |
| WO | 0228473 | 4/2002 |
| WO | 0230507 | 4/2002 |
| WO | 0232498 | 4/2002 |
| WO | 02/43623 | 6/2002 |
| WO | 0243623 | 6/2002 |
| WO | 02094334 | 11/2002 |
| WO | 03049658 | 6/2003 |
| WO | 2004002570 | 1/2004 |
| WO | 2007/027879 | 3/2007 |
| WO | 2007002879 A1 | 3/2007 |
| WO | 2007027879 | 3/2007 |
| WO | 2009065127 A1 | 5/2009 |
| WO | 2009065171 A1 | 5/2009 |
| WO | 2009079704 A1 | 7/2009 |
| WO | 2010015016 A1 | 2/2010 |
| WO | 2010015017 A1 | 2/2010 |
| WO | 2010091237 A2 | 8/2010 |
| WO | 2010091237 A3 | 11/2010 |

OTHER PUBLICATIONS

Kha et al., Stiffness Properties of Nucleus Standard Straight and Contour Electrode Arrays, Med and Eng Phys 26 677-685, 2004.

Reuter, G. et al., "Fine tuning of cochlear implant materials—cell interactions by femtosecond laser microstructuring." European Cells and Materials vol. 13. Suppl. 3, 2007 (p. 10).

He, Bo et al., Surface Texture effect on Friction of a Microtextured Polydimethylsiloxane, Tribology Letters, vol. 31, No. 3, Aug. 12, 2008; pp. 1-11.

Stover, Timo et al., "Microstructured Cochlear implant electrodes," Subproject T1 of Collaborative Research Center 599; pp. 1-2; Feb. 7, 2011.

Lenarz, Thomas et al., "Nerve-Electrode Interface," Subproject D2 of Collaborative Research Center 599; pp. 1-2; Feb. 7, 2011.

* cited by examiner

```
┌─────────────────────────────────────────────────────┐
│ Inserting a stiffening stylet into a lumen of the   │
│ electrode array.                                    │
│ (step 805)                                          │
└─────────────────────────────────────────────────────┘
                          │
┌─────────────────────────────────────────────────────┐
│ While maintaining the stylet within the lumen and   │
│ in a fixed position with respect to the electrode   │
│ array, inserting the electrode array through a      │
│ cochleostomy into the cochlea such that when the    │
│ electrode array is fully inserted in the cochlea,   │
│ the stylet extends approximately 8 to 9 millimeters │
│ into the cochlea as measured from the cochleostomy. │
│ (step 810)                                          │
└─────────────────────────────────────────────────────┘
                          │
┌─────────────────────────────────────────────────────┐
│ After full insertion of the electrode array into    │
│ its final position within the cochlea, the stylet   │
│ is withdrawn from the lumen.                        │
│ (step 815)                                          │
└─────────────────────────────────────────────────────┘
```

*Fig. 8*

COCHLEAR IMPLANT SYSTEM WITH REMOVABLE STYLET

BACKGROUND

Hearing loss can be corrected using a number of approaches, including the use of a cochlear implant. A cochlear implant includes an electrode array which is surgically implanted into the cochlea of the patient. The electrode array presents electrical stimulation directly to auditory nerve fibers in the cochlea. This leads to the perception of sound in the brain and provides at least partial restoration of hearing function. To minimize damage to sensitive tissues within the patient's cochlea, it can be desirable for the electrode array to be accurately placed within the cochlea using a minimum amount of insertion force.

BRIEF DESCRIPTION OF THE DRAWINGS

The accompanying drawings illustrate various embodiments of the principles described herein and are a part of the specification. The illustrated embodiments are merely examples and do not limit the scope of the claims.

Throughout the drawings, identical reference numbers designate similar, but not necessarily identical, elements.

DETAILED DESCRIPTION

In human hearing, hair cells in the cochlea respond to sound waves and produce corresponding auditory nerve impulses. These nerve impulses are then conducted to the brain and perceived as sound.

Hearing loss, which may be due to many different causes, is generally of two types: conductive and sensorineural. Conductive hearing loss typically occurs where the normal mechanical pathways for sound to reach the hair cells in the cochlea are impeded, for example, from damage to the ossicles. Conductive hearing loss may often be helped by using conventional hearing aids that amplify sounds so that acoustic information can reach the cochlea and the hair cells. Some types of conductive hearing loss are also treatable by surgical procedures.

Many people who are profoundly deaf, however, have sensorineural hearing loss. This type of hearing loss can arise from the absence or the destruction of the hair cells in the cochlea which then no longer transduce acoustic signals into auditory nerve impulses. Individuals with sensorineural hearing loss may be unable to derive significant benefit from conventional hearing aid systems alone, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural deafness, cochlear implant systems, or cochlear prostheses, have been developed that can bypass the hair cells located in the cochlea by presenting electrical stimulation directly to the auditory nerve fibers. This leads to the perception of sound in the brain and provides at least partial restoration of hearing function. Most of these cochlear prosthesis systems treat sensorineural deficit by stimulating the ganglion cells in the cochlea directly using an implanted lead that has an electrode array. Thus, a cochlear prosthesis operates by directly stimulating the auditory nerve cells, bypassing the defective cochlear hair cells that normally transduce acoustic energy into electrical activity to the connected auditory nerve cells.

A cochlear implant system typically comprises both an external unit that receives and processes ambient sound waves and a cochlear implant that receives data from the external unit and uses that data to directly stimulate the auditory nerve. In a typical cochlear implant, a microphone receives sound and converts it into electrical signals. These electrical signals are transmitted to a processor implanted in the patient's body and connected to a lead having an electrode array implanted within one of the cochlear ducts, such as the scala tympani. The processor separates acoustic signals into a number of parallel channels of information, each representing a narrow band of frequencies within the perceived audio spectrum. Ideally, each channel of information should be conveyed selectively to a subset of auditory nerve cells that normally transmit information about that frequency band to the brain. Those nerve cells are arranged in an orderly tonotopic sequence, from the highest frequencies at the basal end of the cochlear spiral to progressively lower frequencies towards the apex. The processor then sends the appropriate channels of information to one or more of the electrode contacts, which then generate electrical fields which stimulate the desire subset of auditory nerve cells. This provides the patient with a sense of hearing.

To minimize damage to sensitive tissues within the patient's cochlea, it can be desirable that the electrodes are accurately placed within the cochlea using a minimum amount of insertion force. The cochlear implant should be designed so that the insertion forces do not kink or otherwise damage the delicate wires and electrodes contained within the implant.

According to one illustrative embodiment, the portion of the lead that is inserted into the cochlea can be constructed from biocompatible silicone, platinum-iridium wires, and platinum electrodes. The portion of the lead to be inserted into the cochlea is designed to be relatively flexible so that it can curve around the helical interior of the cochlea. A lumen may be formed through a portion of the cochlear lead. During insertion of the cochlear lead into the cochlea, a stylet may be inserted into the lumen to provide the desired level of rigidity and control during the procedure. For example, the stylet may provide additional rigidity in the basal portion of the lead, thereby reducing the likelihood that the insertion forces will kink the lead. Additionally, the stylet provides the surgeon with greater control over the angle and placement of the lead within the cochlea. Following the full insertion of the cochlear lead, the stylet is retracted from the lumen. This leaves the cochlear lead in position in the cochlea without an internal stiffening element. Because the cochlear lead is relatively compliant, the forces that the cochlear lead exert on the interior of the cochlea during use can be substantially less than cochlear leads which retain an internal stiffening element.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "an embodiment," "an example," or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

Figure 1:
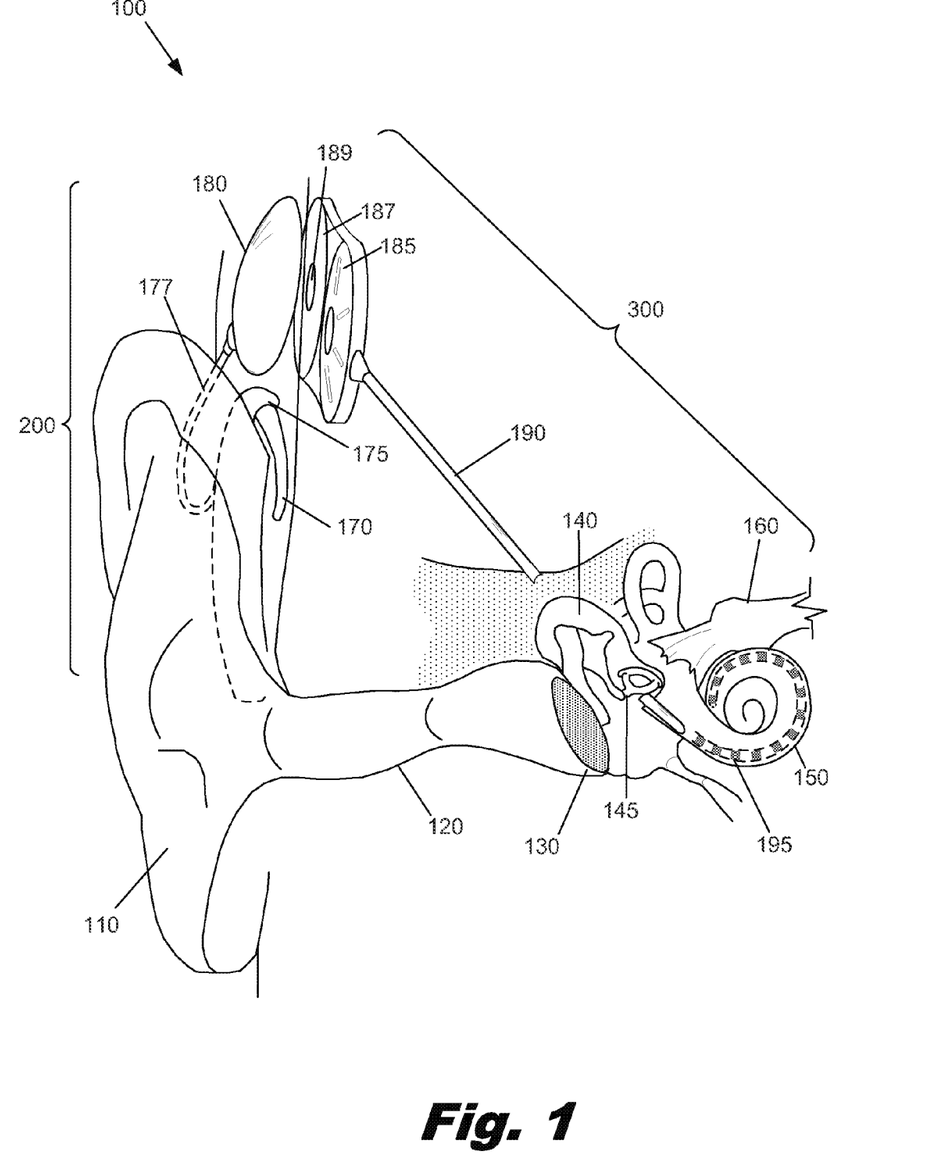
FIG. 1 is a diagram showing an illustrative cochlear implant system in use, according to one embodiment of principles described herein.

FIG. 1 is a diagram showing one illustrative embodiment of a cochlear implant system (100) having a cochlear implant (300) with an electrode array (195) that is surgically placed within the patient's cochlea. Ordinarily, sound enters the external ear, or pinna, (110) and is directed into the auditory canal (120) where the sound wave vibrates the tympanic membrane (130). The motion of the tympanic membrane is amplified and transmitted through the ossicular chain (140), which consists of three bones in the middle ear. The third bone of the ossicular chain (140), the stirrup (145), contacts the outer surface of the cochlea (150) and causes movement of the fluid within the cochlea. Cochlear hair cells respond to the fluid-borne vibration in the cochlea (150) and trigger neural electrical signals that are conducted from the cochlea to the auditory cortex by the auditory nerve (160).

As indicated above, the cochlear implant (300) is a surgically implanted electronic device that provides a sense of sound to a person who is profoundly deaf or severely hard of hearing. In many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide no benefit to persons suffering from complete sensorineural hearing loss.

Unlike hearing aids, the cochlear implant (300) does not amplify sound, but works by directly stimulating any functioning auditory nerve cells inside the cochlea (150) with electrical impulses representing the ambient acoustic sound. Cochlear prosthesis typically involves the implantation of electrodes into the cochlea. The cochlear implant operates by direct electrical stimulation of the auditory nerve cells, bypassing the defective cochlear hair cells that normally transduce acoustic energy into electrical energy.

External components (200) of the cochlear implant system can include a Behind-The-Ear (BTE) unit (175), which contains the sound processor and has a microphone (170), a cable (177), and a transmitter (180). The microphone (170) picks up sound from the environment and converts it into electrical impulses. The sound processor within the BTE unit (175) selectively filters and manipulates the electrical impulses and sends the processed electrical signals through the cable (177) to the transmitter (180). The transmitter (180) receives the processed electrical signals from the processor and transmits them to the implanted antenna (187) by electromagnetic transmission. In some cochlear implant systems, the transmitter (180) is held in place by magnetic interaction with a magnet (189) in the underlying antenna (187).

The components of the cochlear implant (300) include an internal processor (185), an antenna (187), and a cochlear lead (190) having an electrode array (195). The internal processor (185) and antenna (187) are secured beneath the user's skin, typically above and behind the pinna (110). The antenna (187) receives signals and power from the transmitter (180). The internal processor (185) receives these signals and performs one or more operations on the signals to generate modified signals. These modified signals are then sent through the cochlear lead (190) to the electrode array (195), which is the portion of the cochlear lead (190) that is implanted within the cochlea (150) and provides electrical stimulation to the auditory nerve (160).

The cochlear implant (300) stimulates different portions of the cochlea (150) according to the frequencies detected by the microphone (170), just as a normal functioning ear would experience stimulation at different portions of the cochlea depending on the frequency of sound vibrating the liquid within the cochlea (150). This allows the brain to interpret the frequency of the sound as if the hair cells of the basilar membrane were functioning properly.

The cochlear lead typically comprises an electrode array that is implanted in the scala tympani. The electrode array typically includes several separately connected stimulating electrode contacts, conventionally numbering about 6 to 30, longitudinally disposed on a thin, elongated, flexible carrier. The electrode array is pushed into the scala tympani duct in the cochlea, typically to a depth of about 13 to 30 mm via a cochleostomy or via a surgical opening made in the round window at the basal end of the duct.

In use, the cochlear electrode array delivers electrical current into the fluids and tissues immediately surrounding the individual electrode contacts to create transient potential gradients that, if sufficiently strong, cause the nearby auditory nerve fibers to generate action potentials. The auditory nerve fibers branch from cell bodies located in the spiral ganglion, which lies in the modiolus, adjacent to the inside wall of the scala tympani. The density of electrical current flowing through volume conductors such as tissues and fluids tends to be highest near the electrode contact that is the source of such current. Consequently, stimulation at one contact site tends to selectively activate those spiral ganglion cells and their auditory nerve fibers that are closest to that contact site.

Figure 2:
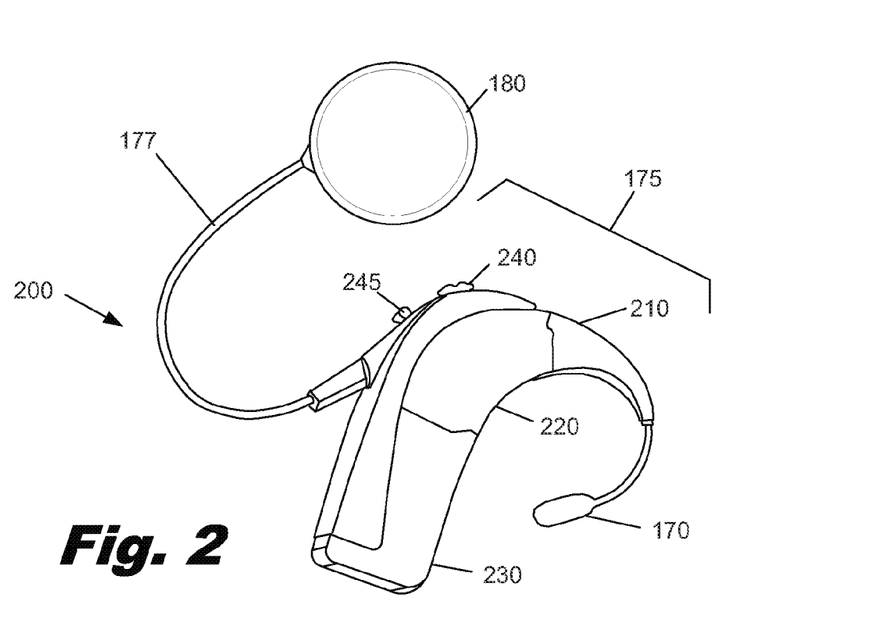
FIG. 2 is a diagram showing external components of an illustrative cochlear implant system, according to one embodiment of principles described herein.

FIG. 2 is an illustrative diagram showing a more detailed view of the external components (200) of one embodiment of a cochlear implant system. External components (200) of the cochlear implant system include a BTE unit (175), which comprises a microphone (170), an ear hook (210), a sound processor (220), and a battery (230), which may be rechargeable. The microphone (170) picks up sound from the environment and converts it into electrical impulses. The sound processor (220) selectively filters and manipulates the electrical impulses and sends the processed electrical signals through a cable (177) to the transmitter (180). A number of controls (240, 245) adjust the operation of the processor (220). These controls may include a volume switch (240) and program selection switch (245). The transmitter (180) receives the processed electrical signals from the processor (220) and transmits these electrical signals and power from the battery (230) to the cochlear implant by electromagnetic transmission.

Figure 3:
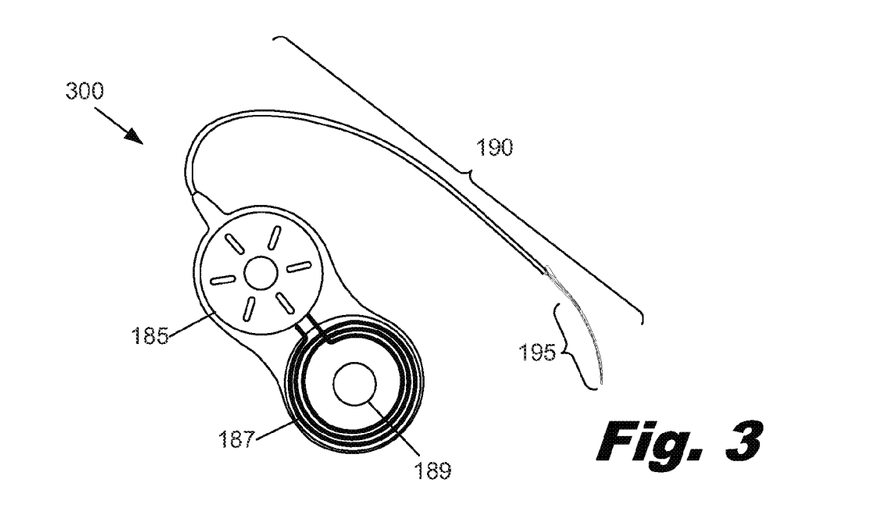
FIG. 3 is a diagram showing internal components of an illustrative cochlear implant system, according to one embodiment of principles described herein.

FIG. 3 is an illustrative diagram showing one embodiment of a cochlear implant (300), including an internal processor (185), an antenna (187), and a cochlear lead (190) having an electrode array (195). The cochlear implant (300) is surgically implanted such that the electrode array (195) is internal to the cochlea, as shown in FIG. 1. The internal processor (185) and antenna (187) are secured beneath the user's skin, typically above and behind the pinna (110), with the cochlear lead (190) connecting the internal processor (185) to the electrode array (195) within the cochlea. According to one illustrative embodiment, the electrode array (195) is straight or slightly curved before being inserted into the cochlea (150). As discussed below, the electrode array (195) is designed for lateral wall placement within the cochlea (150). As discussed above, the antenna (187) receives signals from the transmitter (180) and sends the signals to the internal processor (185). The internal processor (185) modifies the signals and passes them through the cochlear lead (190) to the electrode array (195). The electrode array (195) is inserted into the cochlea and provides electrical stimulation to the auditory nerve. This provides the user with sensory input that is a representation of external sound waves sensed by the microphone (170).

Figure 4A:
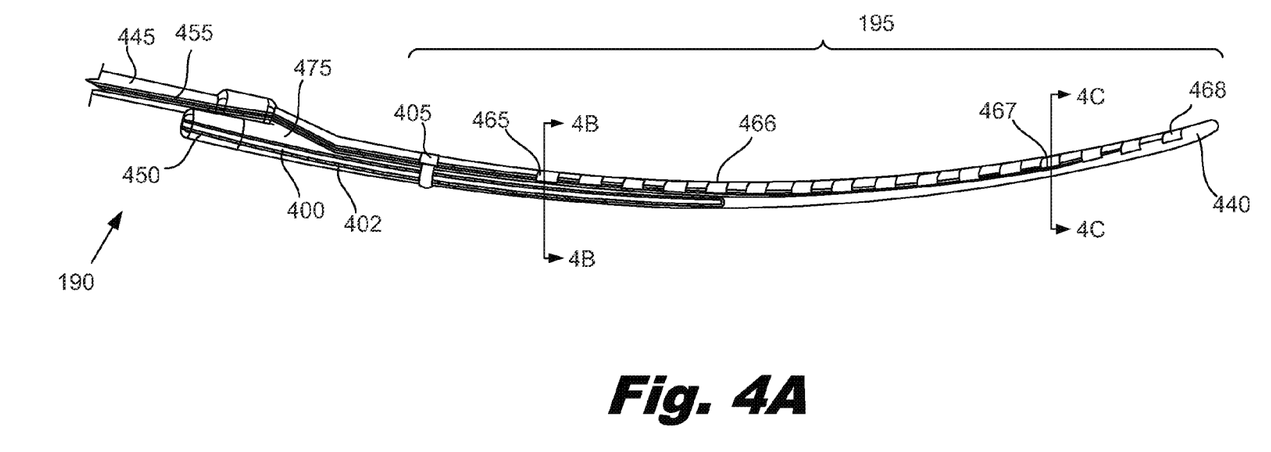
FIG. 4A-4C are diagrams of an illustrative cochlear lead, according to one embodiment of principles described herein.

FIG. 4A is a partial side view of an illustrative cochlear lead (190). The cochlear lead (190) includes an electrode array (195) comprising electrodes (465-468), a lead body (445) carrying wires (455) that extend from the internal processor (185, FIG. 3) to the electrodes, a flexible body (475) on which the electrodes are disposed and having a lumen formed therein, and a molded silicone rubber feature (450). Within the electrode array, the electrodes (465-468) are numbered from the distal tip (440), with the electrode (468) closest to the distal tip (440) being the "first electrode", the adjacent electrode being the "second electrode", and so forth. In this embodiment, there are 16 electrodes, with electrode closest to the basal end of the electrode array being the sixteenth electrode (465). When the electrode array (195) is properly positioned within the cochlea, the cochleostomy marker (405) is positioned at or near the cochleostomy, and the electrodes (465-468) are well positioned to stimulate the tonotopically-arranged groups of nerve endings.

As discussed above, the cochlear lead (190) includes a lead body (445) which connects the electrode array (195) to the internal processor (185, FIG. 3). A number of wires (455) pass through the lead body (445) to bring electrical signals from the internal processor (185, FIG. 3) to the electrode array (195). According to one illustrative embodiment, on the lead body (445), proximal of the electrode array (195), is a molded silicone rubber feature (450). The feature (450) can serve a variety of functions, including, but not limited to, providing a structure that can be gripped or pushed by an insertion tool and providing a visual indicator of how far the cochlear lead (190) has been inserted.

The wires (455) that conduct the electrical signals generated by the processor are connected to the electrodes (465) within the electrode array (195). For example, electrical signals which correspond to a low frequency sound may be communicated via a first wire to an electrode (468) near the tip (440) of the electrode array (195). Electrical signals which correspond to a high frequency sound may be communicated by a second wire to an electrode (465) near the base of the electrode array (195). According to one illustrative embodiment, there may be one wire (455) for each of the electrodes within the electrode array (195). The internal processor (185, FIG. 3) may then control the electrical field generated by each electrode individually. For example, one electrode may be designated as a ground electrode. The remainder of the electrodes may then generate electrical fields which correspond to various frequencies of sound. Additionally or alternatively, adjacent electrodes may be paired, with one electrode serving as a ground and the other electrode being actively driven to produce the desired electrical field.

According to one illustrative embodiment, the wires (455) and portions of the electrodes (465) are encased in a flexible body (475). The flexible body (475) may be formed from a variety of biocompatible materials, including, but not limited to, medical grade silicone rubber. The flexible body (475) secures and protects the wires (455) and electrodes (465). The flexible body (475) allows the electrode array (195) to bend and conform to the geometry of the cochlea. When placed within the cochlea (150), the electrode array (195) is positioned within the scala tympani (420) and brings the individual electrodes into close proximity with the tonotopically organized nerves in the cochlea (150).

According to one illustrative embodiment, a lumen (400) may extend through the flexible body (475) from the molded rubber feature (450) and into the electrode array (195). The illustrative lumen (400) may have a variety of lengths and extend through the electrode array to a variety of locations. As shown in FIG. 4A, the lumen (400) extends slightly past the sixteenth electrode (465). In other embodiments, the lumen may extend to the twelfth electrode (466), or any other electrode in the electrode array (195). A variety of stiffening elements or stylets can be inserted into the lumen (400). For example, if the lumen (400) extends to the twelfth electrode (466), any stiffening element which extends into the lumen less than that distance can be used. According to one illustrative embodiment, the lumen (400) is cylindrical with an inside diameter of approximately 0.004 inches (0.10 mm) and an outside diameter of approximately 0.007 inches (0.18 mm).

The lumen (400) formed within the typically silicone rubber flexible body (475) may be lined with a variety of materials and have a number of different geometries. For example, the lumen (400) may be defined by a lumen liner (402) which is formed from polytetrafluoroethylene (PTFE) or expanded PTFE, both of which are inert, biocompatible, and provide a low coefficient of friction for the stylet to slide within. Expanded PTFE shares these characteristics with unexpanded PTFE but has a number of different physical properties. For example, expanded PTFE may be less dense, have increased porosity, and may be less stiff than unexpanded PTFE. In some embodiments, an expanded PTFE lumen may be filled with a bioactive agent. The characteristics of the expanded PTFE lumen may be configured to control the elution of the bioactive agent out of the lumen.

The geometry of the lumen (400) may change along its length. For example, the lumen (400) may have two or more diameters. In one illustrative embodiment, the lumen (400) extends from the molded feature (450) through a substantial portion of the electrode array (195). The lumen (400) has a larger inside diameter (for example 0.006 inch (0.15 mm) diameter) from the opening of the lumen to the twelfth electrode (466) and then a smaller diameter (for example, a 0.003 inch (0.08 mm) diameter) through the remainder of the lumen. Consequently, a stiffening element which has a diameter of approximately 0.004 (0.10 mm) inches to 0.006 (0.15 mm) can be inserted into the lumen (400) to the twelfth electrode (466). A smaller diameter stiffening element may be inserted deeper into the lumen (400).

The lumen liner (402) may have an open or closed distal end. Where the lumen liner (402) has a closed distal end, the material that makes up the lumen liner forms the end of the lumen. Where the lumen liner (402) has an open end, the silicone rubber that forms the flexible body (475) forms the end of the lumen and may extend into the end of the lumen liner.

Figure 4B:
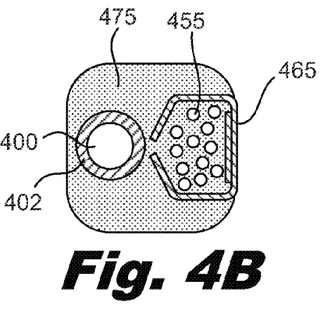

FIG. 4B shows a cross-section along line 4B-4B of a portion of the illustrative cochlear lead (190) in which the lumen liner (402) is disposed. The interior of the lumen liner (402) defines the lumen (400). The wires (455) may be shaped into a wire bundle by the electrode (465). Portions of the electrode, the wires, and the lumen liner (402) are encapsulated by the flexible body (475). In this particular embodiment, the electrodes (465-468) are disposed within the flexible body (475) along one side of the electrode array (195). The lumen liner (402) is disposed in flexible body (475) opposite the electrodes (465-468).

Figure 4C:
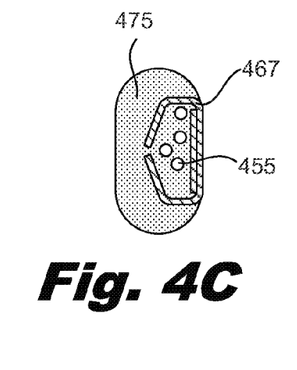

FIG. 4C is a cross-sectional diagram along line 4C-4C, which is located at a more distal location along the cochlear lead (190) and intersects the fourth electrode (467). In this illustrative embodiment, the fourth electrode (467) has a lower profile and contains a reduced number of wires (455) than the sixteenth electrode (465) shown in FIG. 4B. In this embodiment, the lumen (400) does not extend into the distal end of the cochlear lead (190). As shown in the present embodiment, the distal end of the cochlear lead (190) may be flattened, thinned, or the shape or dimensions otherwise modified to allow it to be more flexible than the rest of the lead. The more distal electrodes (467, 468) within the flattened portion of the lead may be appropriately sized so as to fit and function effectively within the reduced cross-section. Additionally, any other components within the flattened or size-reduced portion of the lead can be appropriately sized to fit within the cross-section.

Figure 5A:
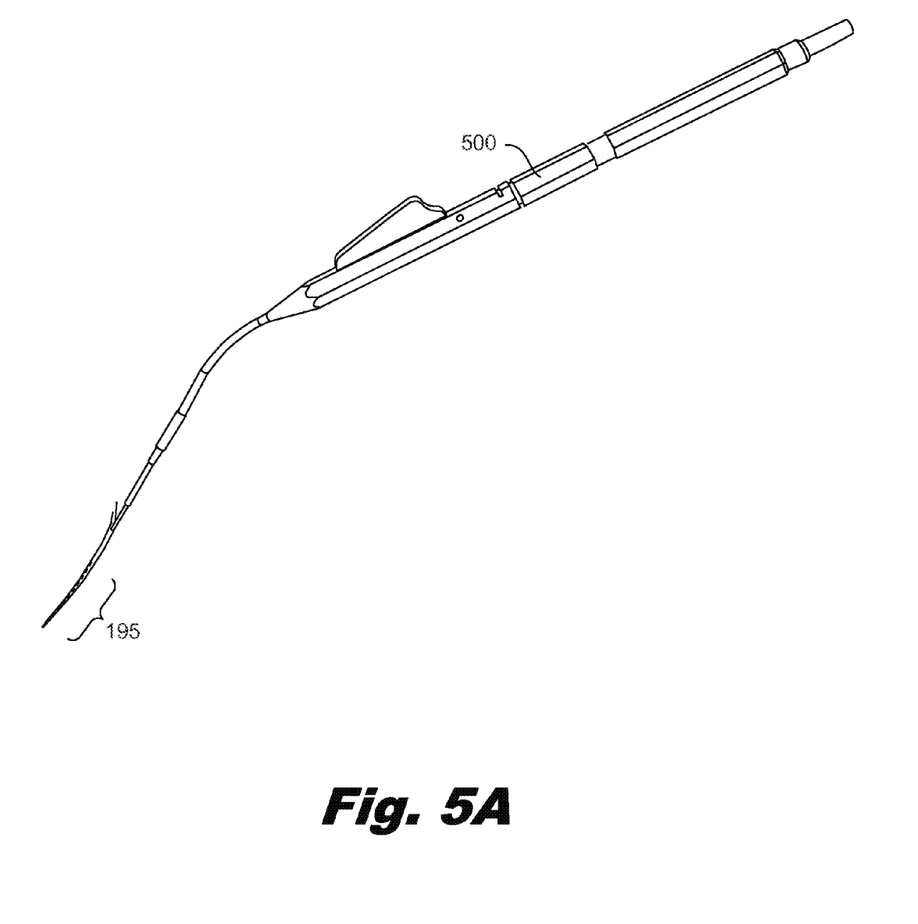
FIG. 5A is a diagram of an illustrative insertion tool which is interfaced to a cochlear lead, according to one embodiment of principles described herein.

FIG. 5A is a diagram of an illustrative insertion tool (500), which may be used to insert the electrode array (195) into a patient's cochlea. On the distal end of the insertion tool (500), insertion tool (500) is detachably connected to the electrode array (195). The insertion tool (500) may incorporate a number of features which allow the electrode array (195) to be manipulated during the insertion procedure. For example, one feature of the insertion tool (500) may be an integral stylet that is inserted into the lumen (400) in the electrode array (195). In other embodiments, the stylet may be separate from the insertion tool (500). The separate stylet is inserted into the lumen (400) of the electrode array (195) and then attached to the insertion tool (500).

Figure 5B:
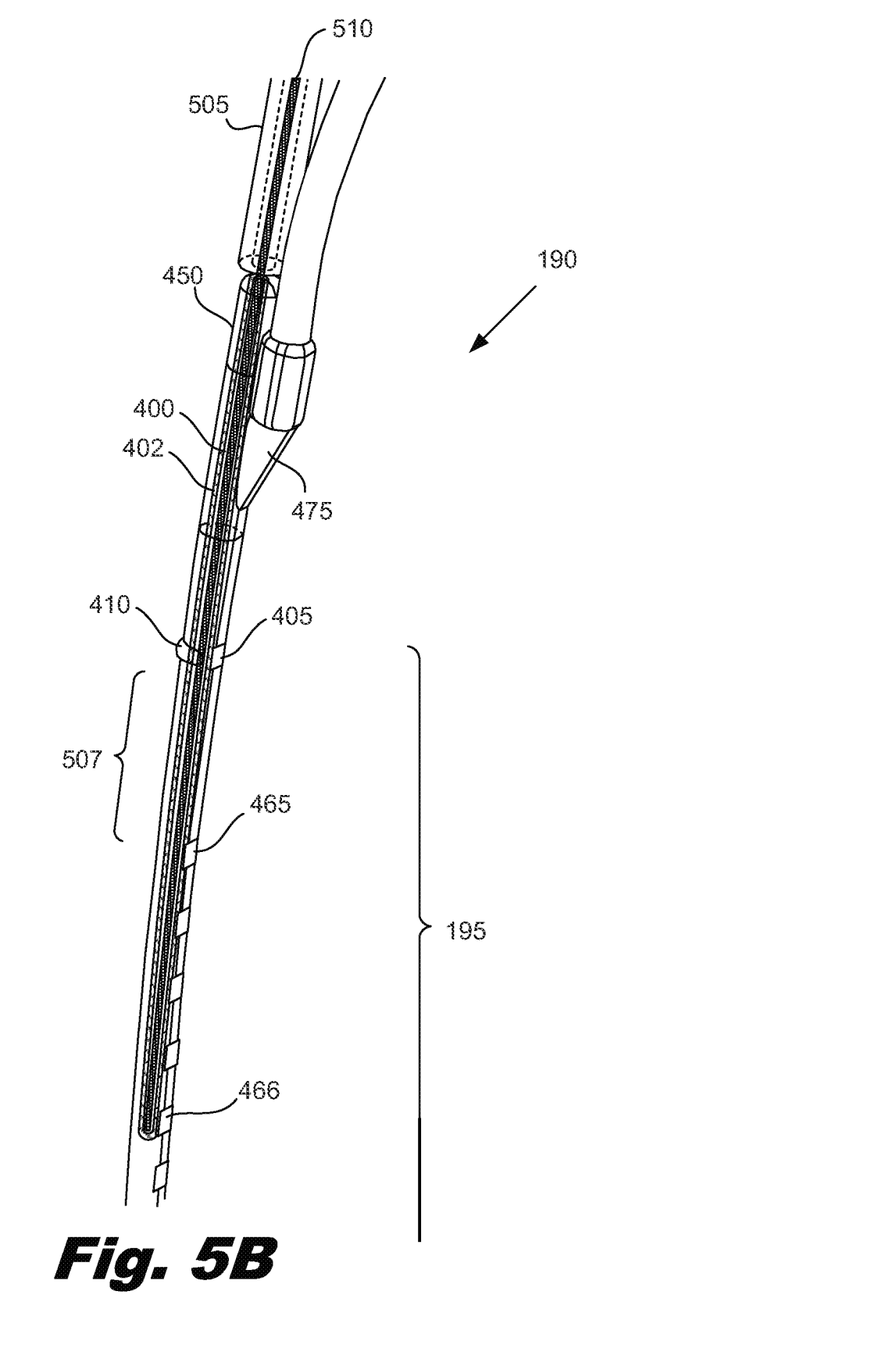
FIG. 5B is a diagram of an illustrative interface between an insertion tool and a cochlear lead, according to one embodiment of principles described herein.

FIG. 5B shows an illustrative interface between the insertion tool (500, FIG. 5A) and the electrode array (195). For purposes of illustration, a number of other attachment mechanisms between the insertion tool (500, FIG. 5A) and the electrode array (195) have not been shown in FIG. 5B. An example of portions of the insertion tool (500, FIG. 5A) which are not illustrated may be an interface with the electrode array (195) to control the rotation of the electrode array (195) around a longitudinal axis that passes along the length of the electrode array (195). One illustrative example of an insertion tool and corresponding electrode is described in U.S. patent. application. Ser. No. 12/824,120, entitled "Tools, Systems, and Methods for Inserting an Electrode Array Portion of a Lead into a Bodily Orifice,"to Thenuwara et al., filed on Jun. 25 , 2010, which is incorporated herein by reference in its entirety. Another illustrative example of an insertion tool which could be used in conjunction with the cochlear lead described above is described in U.S. patent. application. Ser. No. 12/824,122, entitled "Tools, Systems, and Methods for Inserting an Electrode Array Portion of a Lead into a Bodily Orifice", to Thenuwara et al., filed on Jun. 25, 2010, which is incorporated herein by reference in its entirety. Yet another illustrative example of an insertion tool which could be used in conjunction with the cochlear lead described above is described in U.S. patent. application. Ser. No. 12/824,119, entitled "Tools, Systems, and Methods for Inserting an Precurved Electrode Array Portion of a Lead," to Thenuwara et al., filed on Jun. 25, 2010, which is incorporated herein by reference in its entirety. The cochlear lead (195) and its electrode array (190) may be modified to facilitate the use of a particular insertion tool.

In this illustrative embodiment, the stylet (510) extends from the insertion tool (500, FIG. 5A) through a stabilizing tube (505) and into the lumen (400) in the flexible body (475). In this example, the lumen (400) is formed by a lumen liner (402) which extends through the silicone feature (450) and to the twelfth electrode (466). The stylet (510) makes the proximal portion stiffer, or more rigid, than the distal end of the electrode array (195). According to one illustrative embodiment, the stylet (500) can extend through the portion of the cochlear electrode array (190) which remains substantially straight during and after insertion of the electrode array (190) into the cochlea. This can reduce the likelihood of the electrode array (190) buckling during insertion. Additionally, the stylet (510) allows the electrode array (190) to be manipulated more precisely during the insertion. However, the actual position of the stylet (500) within the cochlear lead (190) is dependent on a number of factors including length of the electrode array, the spacing of the electrodes, the number of electrodes, the planned insertion depth of the electrode array and other factors.

FIG. 5B also shows a cochleostomy marker (405) and marking feature (410). In one embodiment, the cochleostomy marker (405) may be a may have a similar structure as an electrode, but is not electrically connected to a signal wire. The cochleostomy marker (405) is used to provide a visual indication of insertion depth and for wire management within the electrode array (195). Additionally, the cochleostomy marker (405) is also visible in fluoroscope images made during the surgery or post-operation x-ray images. The marking feature (410) is a molded silicone rubber feature which provides a visual indication of the electrode array (195) insertion depth during the implantation surgery.

The stylet (510) may be made of any material that provides the desired mechanical and chemical properties. By way of example and not limitation, the stylet (510) may be a plastic, metal, glass, composite, or other material. According to one embodiment, the stylet (510) is formed from platinum or platinum alloy. For example, the stylet (510) may be formed from a platinum iridium alloy. Alternatively, the stylet (510) may be formed from a stainless steel such as 304 series stainless steel, gold, gold alloys, titanium, or titanium alloys such as Nitinol.

The stylet (510) may have a variety of cross sectional geometries. According to one illustrative embodiment, the stylet (510) has a circular cross section with a diameter between 0.08 millimeters (0.003 inches) and 0.15 millimeters (0.006 inches).

In some embodiments, the physical properties of the stylet (510) may vary along its length. For example, the tip or distal portion of the stylet (510) may have different properties than the body of the stylet. By making the tip of the stylet (510) more compliant than the body of the stylet, the possibility of the stylet (510) puncturing lumen (400) is reduced. For example, the distal portion (507) of the stylet (510) with altered physical properties may have a length of approximately 2 to 6 millimeters. In some embodiments, the distal portion (507) of the stylet (510) may be annealed while the body portion of the stylet (510) is not annealed. In other embodiments, the geometry of the distal portion (507) of the stylet (510) may be altered to reduce its stiffness. A number of approaches to reducing the stiffness of portions of a stylet are discussed in U.S. patent. application. Ser. No. 12/789,264, to Chuladatta Thenuwara, entitled "Cochlear Lead" which is incorporated herein by reference in its entirety. As discussed in the reference above, the stiffness of the tip can be altered by annealing, changing the geometry, changing materials, work hardening, micromachining features in the tip, selectively applying coatings, or other techniques.

Figure 6A:
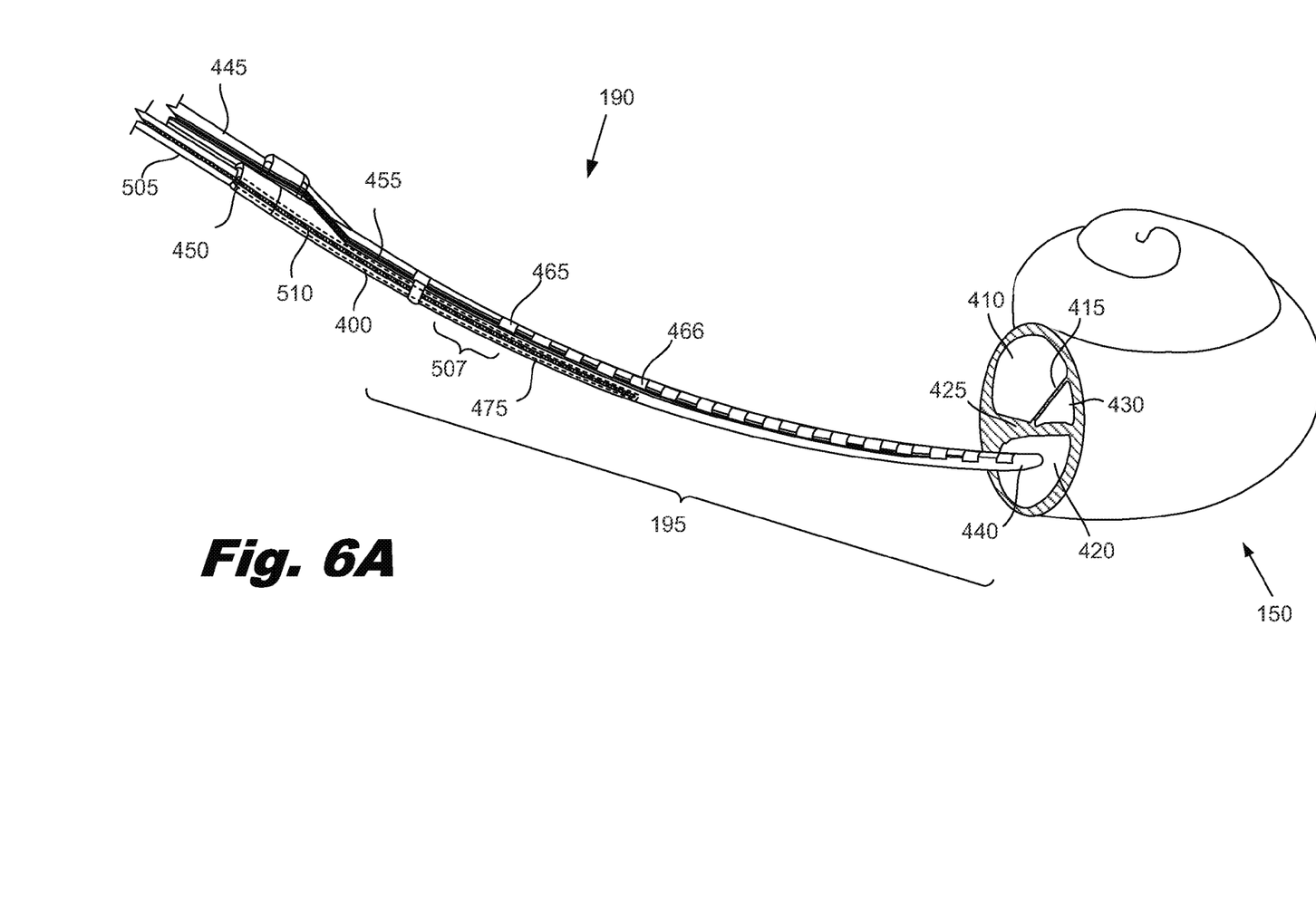
FIG. 6A-6D are diagrams of an illustrative cochlear lead being inserted into a cochlea, according to one embodiment of principles described herein.

FIG. 6A is a partially cut away perspective view of a cochlea (150) and shows an illustrative electrode array (195) being inserted into the cochlea (150). The primary structure of the cochlea is a hollow, helically coiled, tubular bone, similar to a nautilus shell. The coiled tube is divided through most of its length into three fluid-filled spaces (scalae). The scala vestibuli (410) is partitioned from the scala media (430) by Reissner's membrane (415) and lies superior to it. The scala tympani (420) is partitioned from the scala media (430) by the basilar membrane (425) and lies inferior to it. A typical human cochlea includes approximately two and a half helical turns of its constituent channels. The cochlear lead (190) is inserted into one of the scalae, typically the scala tympani (420), to bring the individual electrodes into close proximity with the tonotopically organized nerves.

As shown in FIG. 6A, the electrode array (195) is relatively straight or has a slight curvature prior to insertion into the cochlea. For example, the electrode array (195) may have a radius of curvature of approximately 20-50 millimeters in its relaxed state. As used in the specification and appended claims, the term "substantially straight" refers to an electrode array which has a radius of curvature of greater than 20 millimeters in its relaxed state.

Additionally, as was previously shown in FIG. 5B, a stylet (510) may be inserted into the lumen (400), which is shown with dashed lines in a portion of the lead proximal of the electrode array (195). Placing the stylet (510) into the lumen (400) does not substantially alter the geometry of the electrode array (195), e.g., it does not change its geometry from spiral to straight. According to one illustrative embodiment, the lumen (400) passes through a molded silicone rubber feature (450). The stylet (510) allows the cochlear lead to be more precisely positioned within the cochlea and reduces the propensity of the cochlear lead (190) to buckle. As discussed above, the stylet (510) may have a tip (507) that is more flexible and/or more compliant than the remainder of the stylet (510). According to one illustrative embodiment, the tip (507) has an overall length of approximately 2 to 6 millimeters. This flexible tip (507) can reduce the likelihood that the stylet (510) will puncture the lumen (400) or cause damage to tissues within the cochlea (150).

Figure 6B:
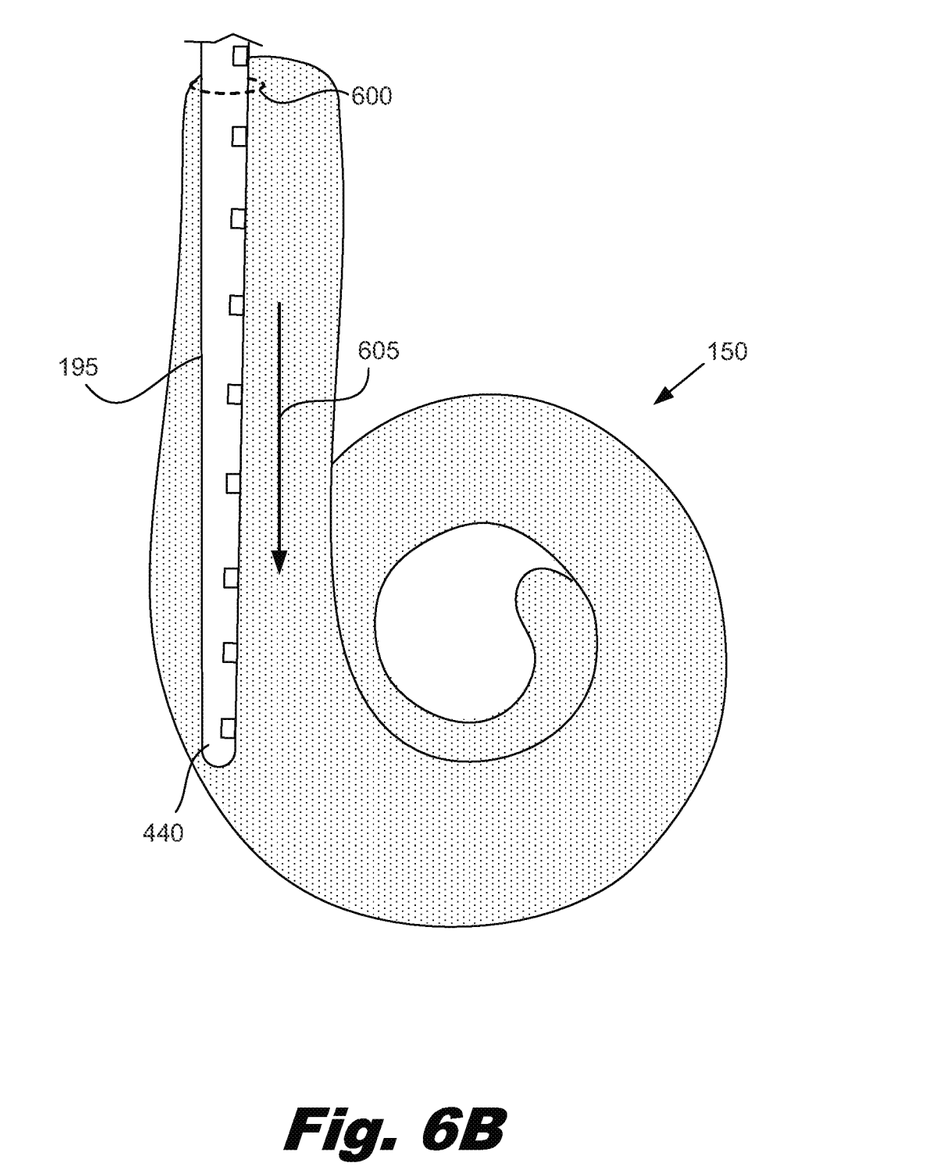
Figure 6C:
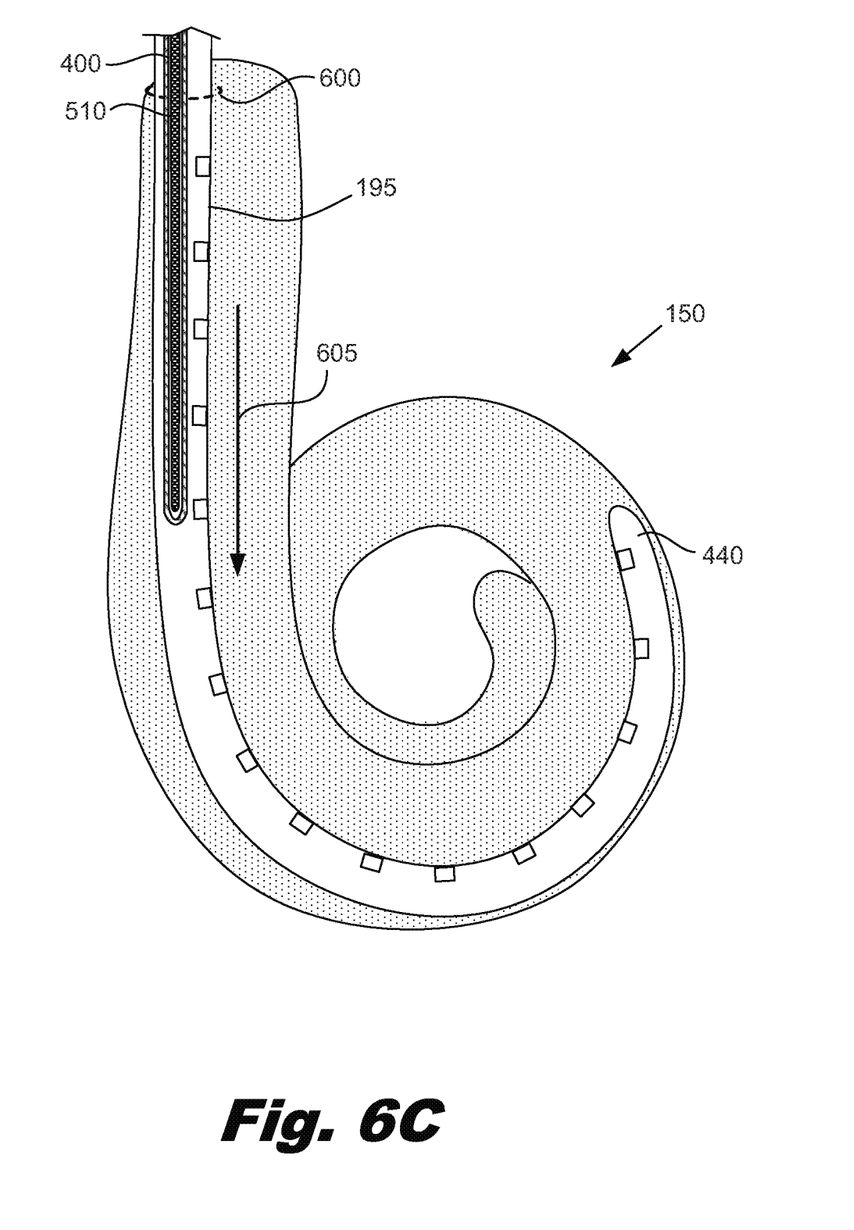
Figure 6D:
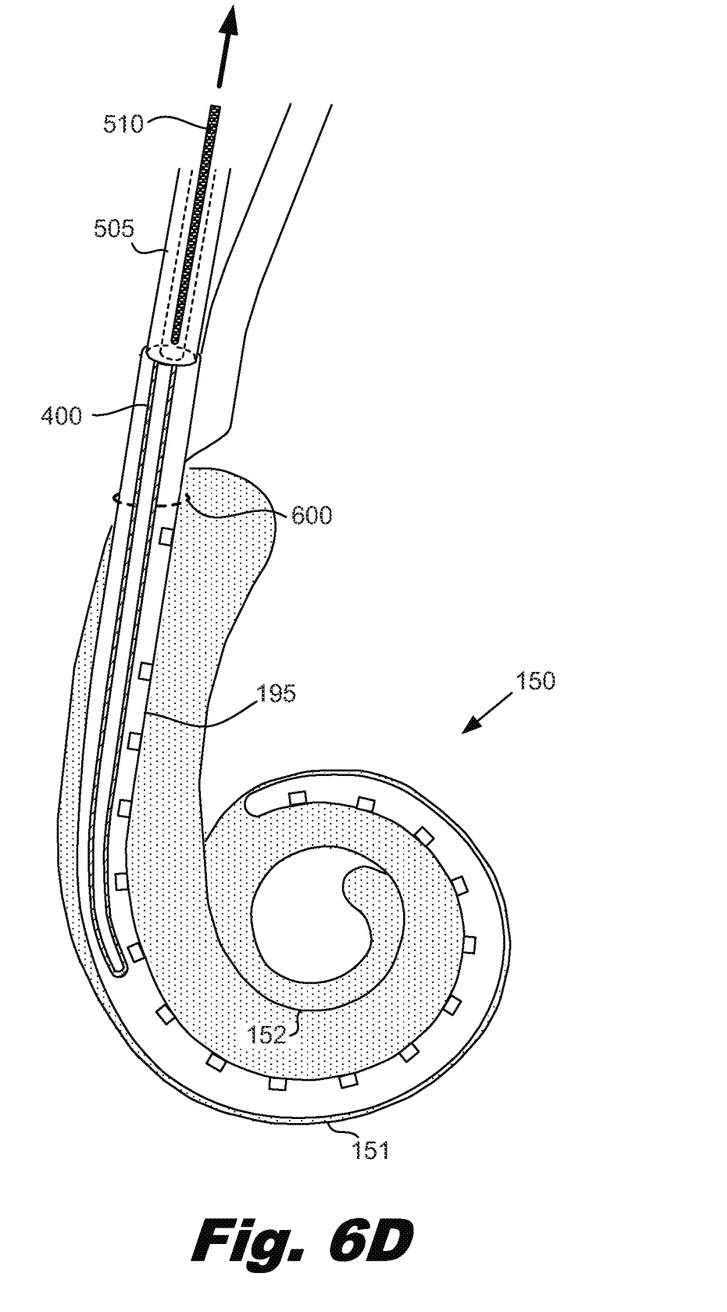

As illustrated in FIG. 6A, the stylet (510) is designed to be inserted completely into lumen (400) prior to insertion of the electrode array (195) into the cochlea (150). FIGS. 6B-6D show the progressive insertion of the electrode array (195) into the cochlea and the withdrawal of the stylet (510) from the lumen (400) after the electrode array (195) is in its final position.

FIG. 6B shows a cutaway view of a cochlea, showing the electrode array (195) with a stylet (510, FIG. 6A) placed into the lumen (400, FIG. 6A) being inserted into a cochlea (150). The electrode array (195) is inserted into the cochlea (150) through a cochleostomy (600) by an axial insertion force (605). In FIG. 6B, the stylet (505) is not yet visible.

FIG. 6C shows the electrode array (195) continuing to be inserted into the cochlea (150) and the stylet (510) just beginning pass through the cochleostomy (600). In some embodiments, the stylet (510) and lumen (400) may be configured so that the stylet extends from 8 to 10 millimeters into the cochlea (150) as measured from the cochleostomy (600) when the electrode array (195) is fully inserted.

FIG. 6D shows the electrode array (195) in its final position and the stylet (510) being retracted out of the lumen (400). As shown in FIG. 6D, the lumen (400) and stylet (510) extend into the cochlea only in the relatively straight portion of scala tympani. Retracting the stylet (510) from the lumen (400) has a number of benefits, including reducing the forces exerted by the electrode array (195) over time. When stylets remain within an electrode array after insertion, the stiffness of stylets can cause the electrode array to exert pressure on the walls of the cochlea. By removing the stylet (510), the electrode array (195) becomes much more compliant and exerts less force on the cochlea during its lifetime.

In FIG. 6D, the cochlear electrode (190) is shown in a position which is primarily adjacent the lateral wall (151) of the cochlea (150). However, the cochlear electrode (190) could be placed in the cochlea in adjacent the medial wall (152) or at locations between the medial wall (152) and the lateral wall (151).

Although the description above describes an illustrative embodiment in which an insertion tool is used, the electrode array could also be placed freehand by the surgeon. To place an electrode array freehand, the surgeon uses more conventional surgical tools to manipulate the electrode array during insertion. In some circumstances, a specialized stylet may be inserted into the lumen and grasped using a convention surgical implement, such as locking forceps.

Figure 7A:
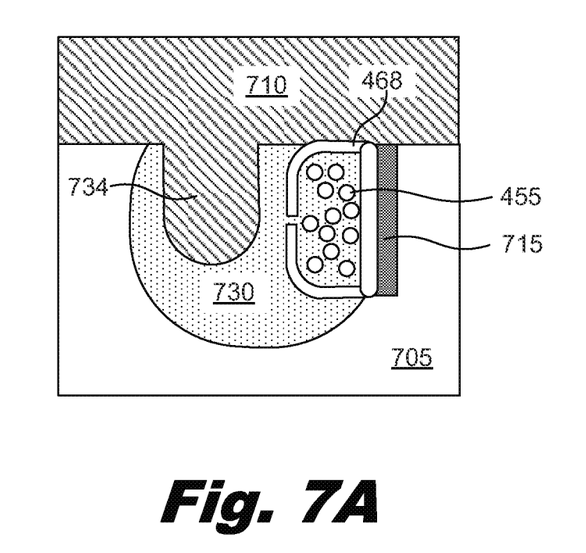
FIGS. 7A-7B are cross sectional diagrams of steps in an illustrative molding process for forming a cochlear lead with an integral lumen, according to one embodiment of principles described herein.
Figure 7B:
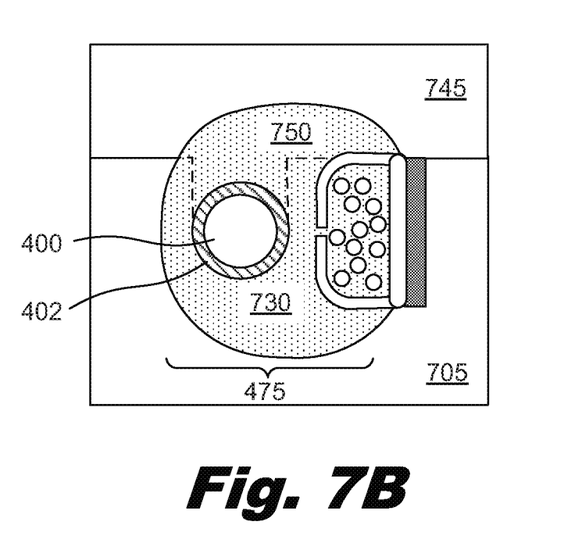

FIGS. 7A-7C are cross sectional diagrams of various illustrative steps in a process for forming a lumen (400) into a cochlear lead (190; FIG. 4A). In one embodiment, the cochlear lead includes a number of electrodes (465) which have wings (468) which extend into the interior of the cochlear lead. These wings (468) form an enclosed space through which the wires (455) pass. During manufacturing, the electrodes (465) are attached to a sacrificial iron strip (715). The sacrificial iron strip (715) holds the electrodes in place during the various manufacturing and molding steps used to form the cochlear lead. After the electrodes are molded into place, the sacrificial strip (715) can be removed.

In FIG. 7A, the sacrificial iron strip (715) and the electrodes (720) attached to the iron strip (715) are placed in the cavity of an insert mold bottom (705) and covered with a mold top (710). According to one illustrative embodiment, the mold top (710) includes a protrusion (734) which extends downward into the cavity formed by the bottom shell (7.05). Medical grade silicone is then injected to fill the cavity and surround the electrode wings (725). The medical grade silicone contacts the back and side portions of the electrode (720), but not the surface of the electrode that is joined to the sacrificial iron strip (715). The medical grade silicone is then cured to form a first portion (730) of the flexible body (475). The mold top (710) is then removed.

FIG. 7B is a cross sectional diagram of the cured first portion (730) of the flexible body, which includes a channel formed by protrusion (734). The lumen liner (402) is placed in the bottom of the channel and a second mold top (745) may be placed over the first portion (730) of the flexible body and more medical grade silicone can be injected into the resulting cavity to fill the channel (735). As discussed above, the interior cavity of the lumen liner (400) defines the lumen (400). This second portion (750) of the medical grade silicone is cured to complete the flexible body and encapsulate the lumen liner (402). A dotted line (740) shows the interface between the first and second portions (730, 750) which form the flexible body (475). The flexible body (475) is then removed from the mold and various additional manufacturing steps can be performed to complete the cochlear implant.

Figure 8:
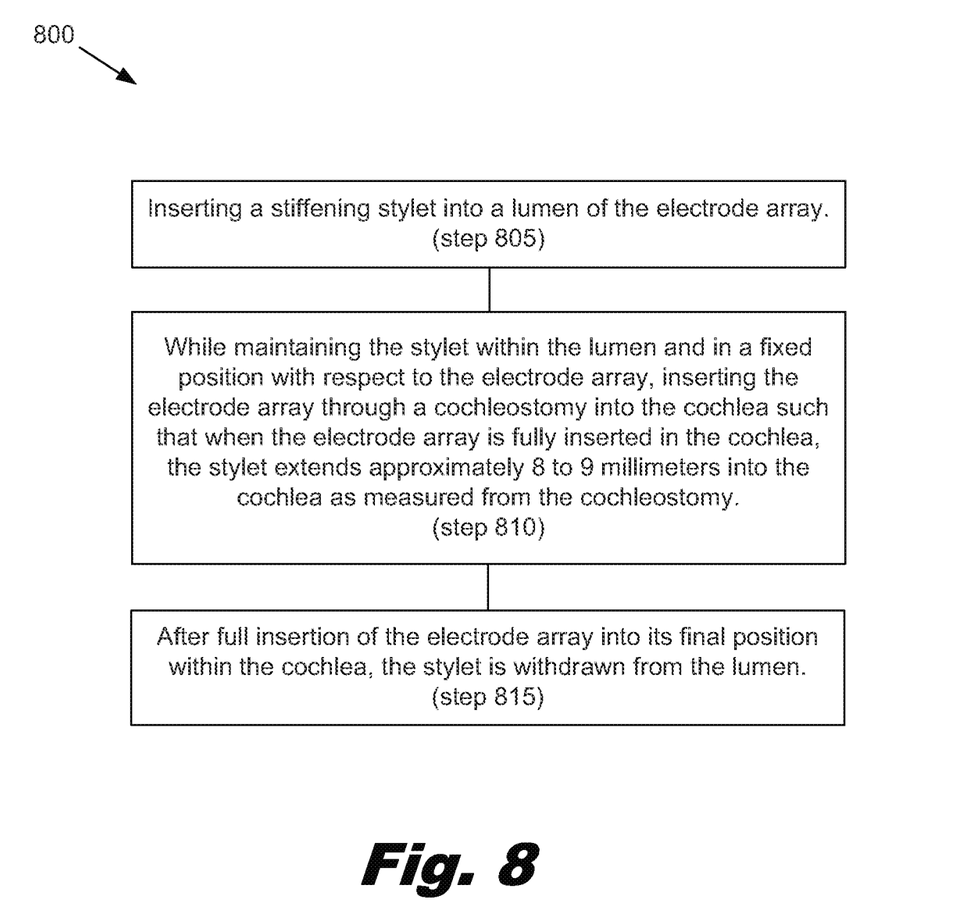
FIG. 8 is a flowchart showing an illustrative method for inserting a cochlear lead into a cochlea, according to one embodiment of principles described herein.

FIG. 8 is a flowchart of one illustrative method (800) for implanting an electrode array into a cochlea. In a first step, the stiffening stylet is inserted into a lumen of the electrode array (step 805). For example, the stiffening stylet may be an integral stylet of an insertion tool. The integral stylet may extend out of the insertion tool and be inserted into the lumen. In an alternative embodiment, the stiffening stylet may be inserted into the lumen and then attached to the insertion tool.

While maintaining the stylet within the lumen and in fixed position with respect to the electrode array, the electrode array is inserted through a cochleostomy into the cochlea such that when the electrode array is fully inserted in the cochlea, the stylet extends approximately 8 to 10 millimeters into the cochlea as measured from the cochleostomy (step 810). For some insertion tools, this insertion may be accomplished using direct manual manipulation of the tool. In other insertion tools, an actuator on the insertion tool may be manipulated to insert the electrode array using the action of the tool.

After full insertion of the electrode array into its final position within the cochlea, the stylet is withdrawn from the lumen (step 815). The withdrawal of the stylet from the lumen can be accomplished manually or using the action of the insertion tool.

In the illustrative method described above, the stylet remains fully inserted into the lumen during the insertion of the electrode array into the cochlea. As used in the specification and appended claims, the phrase "fully inserted into the lumen" describes the stylet being at or near a maximum designed insertion depth within the lumen. This does not mean that the tip of the stylet must reach the end of the lumen. Rather, the stylet is inserted into the lumen to the maximum designed insertion depth and is designed to remain there until the electrode array is in its final position within the cochlea. For example, the lumen may narrow at some point so that the stylet cannot go any deeper into the electrode array. In this example, the stylet would be "fully inserted into the lumen" when progress of the tip of the lumen is impeded by the constriction in the lumen. During insertion of electrode array, the stylet can remain safely at the designed insertion depth and does not require simultaneous removal of the stylet with advancement of the electrode array.

Similarly, the phrase "fully inserted into the cochlea" describes the electrode array being positioned within the cochlea at a final or optimal insertion depth. The phrase "fully inserted into the cochlea" does not mean that the tip of the electrode array has reached the apex of the cochlea. Rather, the electrode array is "fully inserted into the cochlea" when it has reached a desired final position within the cochlea. This final intended position may be marked in a number of ways, including the lining up of a cochleostomy marker with a cochleostomy.

Only when the electrode array is in its final position is the stylet retracted from the lumen. Because the stylet only extends into the relatively straight portion of the cochlea prior to the basal turn, there is no need to advance the electrode off the stylet during the insertion procedure.

The retraction of the stylet may be accomplished in a variety of ways. For example, the stabilizing tube may be extended to hold the electrode array in place while the insertion tool and stylet are being withdrawn. In other embodiments, the stylet may be retracted by a spring force which withdraws the stylet into the stabilizing tube. During this retraction, the stabilizing tube and stylet do not move and hold the electrode array in place. Combinations of stabilizing tube activation and stylet activation can also be used to withdraw the stylet when the electrode is in its final position.

There are a number of advantages to using a removable stylet. First, the stylet may be inserted manually or with the aid of an insertion tool depending on the preference of the surgeon and the circumstances. Second, the stylet prevents the buckling of the basal part of the electrode and facilitates the full insertion of the electrode array into the cochlea. Buckling is particularly undesirable because it can damage the wires and electrodes in the electrode array and cause injuries to the internal structures of the cochlea.

Third, the removal of the stylet may result in a number of advantages. The removal of the stylet from the electrode array eliminates any additional biocompatibility issues because there is no new material introduced into the electrode array. Because the stylet is not permanently placed within the cochlea, there may be more freedom in stylet material selection. The removal of the stylet may also reduce forces exerted by the electrode array on the cochlea over the lifetime of the cochlear implant.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. A cochlear implant system comprising:
 a substantially straight cochlear electrode array comprising a flexible body having a distal end, a plurality of electrodes supported along a length of the flexible body, and a lumen formed in the flexible body; and
 a stiffening stylet configured to:
  be fully inserted into the lumen prior to insertion of the electrode array into the cochlea such that the stylet does not extend to the distal end;
  remain stationary within the lumen and prevent buckling of the electrode array during insertion of the electrode array through a cochleostomy and into the cochlea until the electrode array is fully inserted in the cochlea and the stylet extends approximately 8 to 10 millimeters into the cochlea as measured from the cochleostomy; and
  be withdrawn from the lumen after the electrode array is positioned within the cochlea.

2. The system of claim 1, in which a distal portion of the stylet is less stiff than a proximal portion of the stylet.

3. The system of claim 2, in which the distal portion of the stylet is annealed.

4. The system of claim 2, in which the distal portion of the stylet is annealed and the proximal portion is not annealed.

5. The system of claim 2, in which both the distal and proximal portions of the stylet are annealed; and in which a geometry of the distal portion is altered such that the distal portion is less stiff than the proximal portion of the stylet.

6. The system of claim 2, in which the proximal portion of the stylet has a circular cross section having a diameter between 0.08 millimeters and 0.15 millimeters.

7. The system of claim 2, in which the distal portion of the stylet has a length of approximately 2 to 6 millimeters.

8. The system of claim 2, in which the distal portion of the stylet comprises superelastic nitinol.

9. The system of claim 1, in which the stylet comprises at least one of: stainless steel, titanium, and titanium alloys.

10. The system of claim 1, in which the stylet comprises platinum or a platinum alloy.

11. The system of claim 1, in which the lumen comprises an expanded PTFE tube.

12. The system of claim 1, in which the lumen comprises a tube having an inside diameter of approximately 0.004 inches (0.10 millimeters) and an outside diameter of approximately 0.007 inches (0.18 millimeters).

13. The system of claim 1, in which the lumen and stylet extend into the electrode array no farther than a tenth electrode in a sixteen electrode array, in which the electrodes are numbered from a distal tip of the electrode array, with the first electrode being closest to the distal tip.

14. The system of claim 13, in which the stylet extends into the electrode array to a point between a sixteenth electrode and the tenth electrode.

15. The system of claim 1, in which insertion of the stiffening stylet into the lumen does not substantially alter a relaxed geometry of the electrode array.

16. A method for implanting an electrode array into a cochlea, comprising:
inserting a stiffening stylet into a lumen of the electrode array;
while maintaining the stylet within the lumen and in fixed position with respect to the electrode array, fully inserting the electrode array through a cochleostomy into the cochlea such that the stylet extends approximately 8 to 10 millimeters into the cochlea as measured from the cochleostomy and a distal end of the electrode array extends 13 to 30 millimeters into the cochlea; and
withdrawing the stylet from the lumen by engaging a stabilizing tube with the electrode array after the electrode array is fully inserted.

17. The method of claim 16, in which insertion of the stiffening stylet into the lumen does not substantially alter curvature of the electrode array.

18. The method of claim 16, in which the stiffening stylet is withdrawn from the lumen by simultaneously advancing the stabilizing tube in contact with the electrode array and withdrawing an insertion tool and the stiffening stylet.

19. The method of claim 16, in which the stiffening stylet is withdrawn from the lumen by retracting the stiffening stylet into the stabilizing tube while a stabilizing tube remains stationary and in contact with the electrode array.

20. The method of claim 16, in which the stiffening stylet extends into the electrode array no farther than a tenth electrode in the electrode array, in which the electrodes are numbered from a distal tip of the electrode array, with the first electrode being closest to the distal tip.

21. The method of claim 16, further comprising inserting the stiffening stylet into the array and then attaching the stiffening stylet to an insertion tool.

22. The method of claim 16, in which the stiffening stylet is an integral stylet of an insertion tool.

23. A cochlear implant system comprising:
a cochlear electrode array comprising a flexible body having a distal end, a plurality of electrodes supported along a length of the flexible body, and a lumen formed in the flexible body; and
an insertion tool comprising a stiffening stylet, the stiffening stylet being configured to:
be fully inserted into the lumen prior to insertion of the electrode array into the cochlea such that the stylet does not extend to the distal end;
remain stationary within the lumen and prevent buckling of the electrode array during full insertion of the electrode array through a cochleostomy and into the cochlea, such that the distal end of the flexible body extends 13 to 30 millimeters into the cochlea, and the stylet extends approximately 8 to 10 millimeters into the cochlea as measured from the cochleostomy; and
be withdrawn from the lumen after the electrode array is positioned within the cochlea.

\* \* \* \* \*